(12) United States Patent
Araki et al.

(10) Patent No.: US 8,154,796 B2
(45) Date of Patent: Apr. 10, 2012

(54) MICROSCOPE APPARATUS

(75) Inventors: Makoto Araki, Kanagawa (JP); Hiroshi Sasaki, Tokyo (JP); Tatsuo Nakata, Tokyo (JP); Makio Ueno, Nagano (JP)

(73) Assignee: Olympus Corporation, Tokyo (JP)

( * ) Notice: Subject to any disclaimer, the term of this patent is extended or adjusted under 35 U.S.C. 154(b) by 178 days.

(21) Appl. No.: 11/593,842

(22) Filed: Nov. 7, 2006

(65) Prior Publication Data

US 2007/0109634 A1 May 17, 2007

(30) Foreign Application Priority Data

Nov. 15, 2005 (JP) .................. 2005-330120

(51) Int. Cl.
*G02B 21/06* (2006.01)

(52) U.S. Cl. ...................................... 359/389

(58) Field of Classification Search .......... 359/385, 359/389

See application file for complete search history.

(56) References Cited

U.S. PATENT DOCUMENTS

| | | | |
|---|---|---|---|
| 6,075,643 A * | 6/2000 | Nonoda et al. | 359/385 |
| 6,094,300 A | 7/2000 | Kashima et al. | |
| 6,388,807 B1 | 5/2002 | Knebel et al. | |
| 6,437,913 B1 * | 8/2002 | Kishi | 359/389 |
| 2002/0020800 A1 | 2/2002 | Knebel et al. | |
| 2003/0031596 A1 | 2/2003 | Tanaami | |
| 2003/0197924 A1 | 10/2003 | Nakata | |
| 2005/0012993 A1 * | 1/2005 | Araya | 359/385 |
| 2006/0029523 A1 | 2/2006 | Tanaami | |
| 2007/0035734 A1 | 2/2007 | Muller et al | |
| 2007/0051869 A1 | 3/2007 | Knebel | |

FOREIGN PATENT DOCUMENTS

| | | |
|---|---|---|
| DE | 103 50 918 B3 | 4/2005 |
| EP | 1 093 001 A2 | 4/2001 |
| EP | 1 186 930 A2 | 3/2002 |
| EP | 1 283 416 A2 | 2/2003 |
| JP | 10-123427 A | 5/1998 |
| JP | 10-206742 A | 8/1998 |
| JP | 11-218677 A | 8/1999 |
| JP | 2003-084207 A | 3/2003 |
| JP | 2004-110017 A | 4/2004 |
| JP | 2004-258691 A | 9/2004 |

(Continued)

OTHER PUBLICATIONS

Braeckmans, Kevin et al, "Three-Dimensional Fluorescence Recovery after Photobleaching with the Confocal Scanning Laser Microscope", Biophysical Journal, New York, US, vol. 85, Oct. 2003, pp. 2240-2252, XP-002346209, ISSN: 0006-3495.

(Continued)

*Primary Examiner* — Alessandro Amari
(74) *Attorney, Agent, or Firm* — Holtz, Holtz, Goodman & Chick, PC (57) ABSTRACT

A microscope apparatus that can observe into the interior of a specimen and that can apply an optical stimulus over a wide area within a short period of time is provided. The microscope apparatus comprises at least one observation scanning optical system including a laser light source for emitting observation laser light, an objective lens, and a scanning optical system for two-dimensionally scanning the observation laser light in a predetermined examination plane of the specimen via the objective lens; and at least one stimulus optical system which includes a lamp light source for emitting light having a wavelength used for optical stimulation and which irradiates the specimen with the light emitted from the lamp light source.

4 Claims, 5 Drawing Sheets

FOREIGN PATENT DOCUMENTS

| | | |
|---|---|---|
| JP | 2005-189290 A | 7/2005 |
| JP | 2005-308985 A | 11/2005 |
| JP | 2005-316289 A | 11/2005 |
| WO | WO 2005/096058 A1 | 10/2005 |

OTHER PUBLICATIONS

Japanese Office Action dated May 31, 2011 in counterpart Japanese Application No. 2005-330120.

English translation of a Japanese Office Action dated May 31, 2011 (issued in counterpart Japanese Application No. JP 2005-330120) filed in an Information Disclosure Statement filed Jun. 13, 2011.

Japanese Office Action dated Jan. 10, 2012 issued in counterpart Japanese Application No. 2005-330120.

* cited by examiner

MICROSCOPE APPARATUS

BACKGROUND OF THE INVENTION

1. Field of the Invention

The present invention relates to a microscope apparatus for detecting transmitted light or reflected light from a specimen or fluorescence produced in the specimen, when the surface of the specimen is scanned with illumination light.

This application is based on Japanese Patent Application No. 2005-330120, the content of which is incorporated herein by reference.

2. Description of Related Art

A known scanning laser microscope in the related art includes a stimulus optical system for applying an optical stimulus to a specimen.

For example, Japanese Unexamined Patent Application, Publication No. Hei 10-206742 discloses a scanning laser microscope including a first laser scanning apparatus and a second laser scanning apparatus. The first laser scanning apparatus scans observation laser light, which irradiates the specimen for performing fluoroscopy, within a plane perpendicular to the optical axis. The second laser scanning apparatus moves stimulus laser light for irradiating a plane at an arbitrary position in the specimen with the stimulus laser light.

Another known microscope apparatus in the related art is provided with an observation optical system including a mercury lamp, a first stimulus optical system including a mercury lamp, and a second stimulus optical system including a laser light source. In this apparatus, different optical systems are used for the optical stimulus according to the type of specimen and so on. For example, Japanese Unexamined Patent Application, Publication No. Hei 10-123427 discloses a microscope apparatus that can observe the state of a specimen by displaying on a TV monitor or the like fluorescence produced in the specimen and collected via an observation optical system.

However, when the region to which the stimulus is to be applied is large, the scanning laser microscopes of the related art suffer from the problem that it takes a long time to scan the stimulus region, and thus it is not possible to capture a rapid response.

In addition, because it is not possible to move the observation plane relative to the depth direction of the specimen, they also suffer from the problem that it is not possible to observe the interior of the specimen.

BRIEF SUMMARY OF THE INVENTION

The present invention provides a microscope apparatus that can observe into the interior of a specimen and that can apply an optical stimulus over a wide area in a short period of time.

A first aspect of the present invention is a microscope apparatus comprising at least one observation scanning optical system including a laser light source for emitting observation laser light, an objective lens, and a scanning optical system for two-dimensionally scanning the observation laser light in a predetermined examination plane of the specimen via the objective lens; and at least one stimulus optical system which includes a lamp light source for emitting light having a wavelength used for optical stimulation and which irradiates the specimen with the light emitted from the lamp light source.

According to this configuration, the observation laser light emitted from the laser light source is two-dimensionally scanned within the predetermined observation plane of the specimen by the action of the scanning optical system. Accordingly, it is possible to observe the state of cells and so forth in a desired sectional plane in the specimen. In addition, because the stimulus optical system including the lamp light source that can radiate light over a wide area is used for the optical stimulation, even if the optical stimulation covers a wide area, it is possible to apply the optical stimulus all at once over the entire area. Accordingly, it is possible to apply the optical stimulus effectively in a short period of time.

Because of the above, with the microscope apparatus according to this aspect, it is possible to carry out three-dimensional observation of the specimen with the observation scanning optical system while applying the optical stimulus over a wide area using the light irradiated from the lamp light source.

The observation scanning optical system described above may employ a confocal scanning-type observation optical system using a confocal effect, or it may employ a multiphoton-excitation-type observation optical system which produces multiphoton excitation upon irradiating a specimen with ultrashort pulsed laser light and which acquires the fluorescence produced at that time. In particular, when using the multiphoton-excitation-type observation optical system, it is possible to remove the need for a pinhole or the like in the detection optical system, and therefore, it is possible to achieve high-sensitivity detection. The microscope apparatus of this invention may be provided with both the confocal scanning-type observation optical system and the multiphoton-excitation-type observation optical system.

In the microscope apparatus described above, the stimulus optical system may further include a shutter in a light path between the lamp light source and the specimen.

According to this configuration, by switching between the open and closed states of the shutter, it is possible to effectively block and transmit light from the lamp light source. Accordingly, starting and stopping the optical stimulation of the specimen can be performed extremely easily.

The microscope apparatus described above may further comprise a focusing mechanism for adjusting the distance between the specimen and the objective lens; and a control unit for synchronously controlling the scanning optical system provided in the observation scanning optical system, the shutter provided in the stimulus optical system, and the focusing mechanism.

According to this configuration, because the scanning of the scanning optical system provided in the observation scanning optical system, the opening and closing of the shutter provided in the stimulus optical system, and the motion of the observation plane by the focusing mechanism are carried out in synchronization, it is possible to adjust the observation and optical stimulus timings to the desired timing. Accordingly, it is possible to apply the optical stimulus while observing a desired sectional plane of the specimen. As a result, it is possible to observe a response immediately after the optical stimulus, and it is thus possible to analyze dynamic characteristics of the specimen.

The microscope apparatus described above may further comprise at least one stimulus scanning optical system including a laser light source for emitting laser light used for optical stimulation and a scanning optical system for two-dimensionally scanning the laser light in a predetermined sectional plane of the specimen.

This configuration includes the stimulus optical system that is suited for effectively applying the optical stimulus over a wide area (for example, several tens to several hundreds of micrometers in diameter) and the stimulus scanning optical system that is suited for applying the optical stimulus in a spot (for example, several micrometers in diameter) for a short period of time. Therefore, it is possible to switch the optical system to be used for optical stimulation according to the characteristics of the specimen. Accordingly, it is possible to realize effective optical stimulation using the optimal optical system, depending on the purpose.

Furthermore, not only do the laser light and the light from the light source have different irradiation regions, but they also have different energy densities. Therefore, by providing both functions, it is possible to use different stimulus times, reaction times, and so forth, thus allowing the degrees of freedom of the optical stimulation to be increased.

In the microscope apparatus described above, the stimulus scanning optical system may include a shutter in a light path between the laser light source and the specimen.

According to this configuration, by switching between the open and closed states of the shutter, it is possible to effectively block and transmit the light from the laser light source. Thus, starting and stopping the optical stimulation of the specimen can be performed extremely easily.

In the microscope apparatus described above, the control unit may synchronously control the scanning optical unit provided in the observation scanning optical system, the shutter provided in the stimulus optical system, the shutter provided in the stimulus scanning optical system, and the focusing mechanism.

According to this configuration, the operation of the scanning optical system provided in the observation scanning optical system, the opening and closing of the shutter provided in the stimulus optical system, the opening and closing of the shutter provided in the stimulus scanning optical system, and the motion of the observation plane by the focusing mechanism are performed in synchronization. Therefore, it is possible to adjust the observation and optical stimulus timings to the desired timing. Accordingly, it is possible to apply the optical stimulus to a desired sectional plane while observing that desired sectional plane in the specimen.

The microscope apparatus described above may further comprise a detection optical system for detecting fluorescence produced by irradiating the specimen with the observation laser light, wherein the detection optical system includes a filter for eliminating light in a wavelength band used for the optical stimulus.

In this way, because the detection optical system includes the filter for eliminating light in the wavelength band used for the optical stimulus, it is possible to effectively cut the leakage light from the stimulus optical system. Accordingly, because it is possible to detect only the fluorescence component generated in the specimen, the detection precision can be improved. It is possible to use, for example, a UV-cut filter, an IR-cut filter, or a bandpass filter that transmits fluorescence as the filter described above.

A second aspect of the present invention is a microscope apparatus comprising a lamp light source for emitting observation light; a disk scanning optical system for irradiating a specimen with the observation light via a confocal disk; and at least one stimulus optical system which includes a lamp light source for emitting light having a wavelength used for optical stimulation and which irradiates the specimen with the light.

According to this configuration, because a confocal image can be acquired at high speed, it is possible to obtain the response of an entire sectional plane of the specimen even when the reaction time in response to the optical stimulus is extremely short.

The present invention affords the advantages that it is possible to observe into the interior of a specimen, and it is possible to apply an optical stimulus over a wide area within a short period of time.

DETAILED DESCRIPTION OF THE INVENTION

Embodiments of the present invention will be described below with reference to the drawings.

First Embodiment

Figure 1:
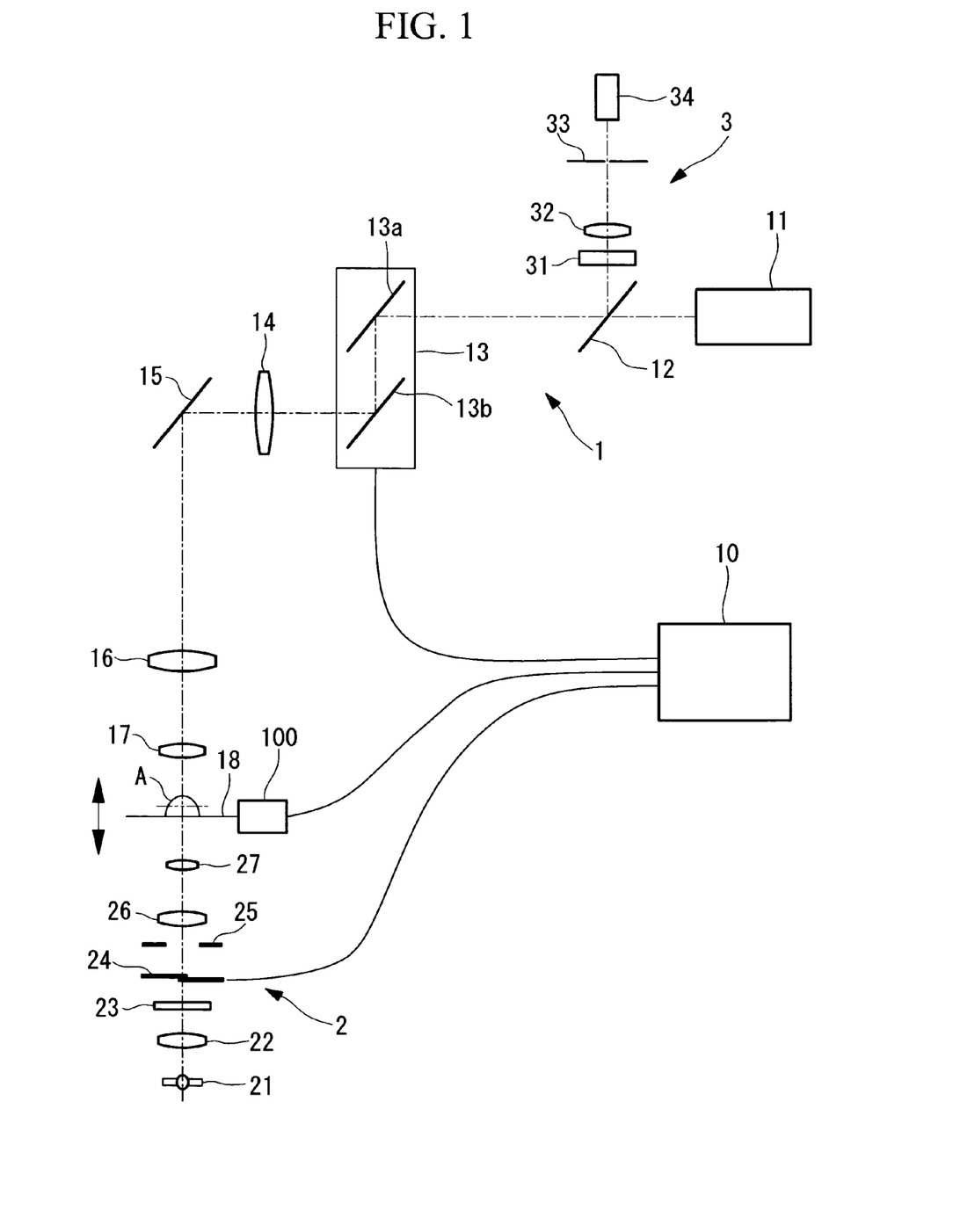
FIG. 1 is a diagram showing, in outline, the configuration of a microscope apparatus according to a first embodiment of the present invention.

FIG. 1 is a block diagram showing, in outline, the configuration of a microscope apparatus according to a first embodiment of the present invention.

The microscope apparatus according to this embodiment includes a confocal observation scanning optical system 1 for irradiating a focal plane on a specimen A with excitation light, used for observing the specimen A, by two-dimensionally scanning the excitation light, and a stimulus optical system 2 for irradiating the specimen A with light for applying a stimulus thereto.

The observation optical system 1 is formed of a laser light source 11, a dichroic mirror 12, a scanning optical unit 13, a relay lens 14, and a mirror 15. The scanning optical unit 13 is a galvanometer scanner formed, for example, of two opposing galvanometer mirrors 13a and 13b which can be oscillated back and forth about mutually orthogonal axes.

An image-forming lens 16 and an objective lens 17 are disposed in the path of the laser beam reflected by the mirror 15. The specimen A is mounted on a stage 18. The stage 18 is constructed so that it can be raised and lowered when driven by a focusing mechanism 100. The focal position of the relay lens 14 is disposed so as to be coincident with the focal position of the image-forming lens 16.

A detection optical system 3 is disposed in the light path split off by the dichroic mirror 12 of the observation scanning optical system 1. This detection optical system 3 is formed of a photometric filter 31, a focusing lens 32, a confocal pinhole 33, and a photoelectric converting device 34. An analog signal output from the photoelectric converting device 34 is transmitted to an analog-to-digital (A/D) converter (not shown in the drawing) where it is converted into digital data and then input to a computer (not shown in the drawing). By creating image data based on luminance data output from the A/D converter and displaying this image data on a monitor, the computer provides the user with the conditions in a desired examination plane in the specimen A.

The stimulus optical system 2 is formed of a lamp light source 21, a collector lens 22, an excitation filter 23, a shutter 24 for blocking and transmitting the light traveling towards the specimen A, a variable aperture 25 for restricting the irradiated region, a focusing lens 26, and a condenser lens 27.

The lamp light source 21 is, for example, a mercury lamp, a xenon lamp, a halogen lamp, a flashlamp, an LED light source, or the like. A filter having a characteristic according to a reagent used in the examination is employed as the excitation filter 23; for example, when using a caged reagent, the excitation filter 23 has a characteristic that allows light with wavelengths ranging from 300 to 400 nm to be transmitted.

Reference numeral 10 in FIG. 1 is a control unit for synchronously controlling the scanning optical unit 13 of the observation scanning optical system 1, the shutter 24 of the stimulus optical system 2, and the focusing mechanism 100.

When examining the specimen A with the microscope apparatus having such a configuration, laser light (hereinafter referred to as observation laser light) is emitted from the laser light source 11. This observation laser light is guided to the scanning optical unit 13 via the dichroic mirror 12 and is deflected in an arbitrary direction. After passing along a path via the relay lens 14, the mirror 15, the image-forming lens 16, and the objective lens 17, the observation laser light is focused onto a sectional plane of the specimen A secured on the stage 18 and is two-dimensionally scanned within the sectional plane.

A fluorescent indicator which is excited by the wavelength of the observation laser light is introduced into the specimen A in advance, and by two-dimensionally scanning the observation laser light within the sectional plane, the fluorescent indicator is excited and produces fluorescence. The fluorescence collected by the objective lens 17 travels backwards along the same optical path as the observation laser light described above, that is, via the objective lens 17, the image-forming lens 16, the mirror 15, the relay lens 14, and the scanning optical unit 13, and is guided to the dichroic mirror 12. The dichroic mirror 12 has a characteristic such that it reflects wavelengths longer than the wavelength of the observation laser light; therefore, the fluorescence is reflected by the dichroic mirror 12 and is introduced into the detection optical system 3.

In the detection optical system 3, light of a specific wavelength in the fluorescence is selectively transmitted by the photometric filter 31. Then, only light coming from the sectional plane is selected by the focusing lens 32 and the confocal pinhole 33 and is incident on the photoelectric converting device 34, where it is converted to an electrical signal. The output signal from the photoelectric converting device 34 is converted to a digital signal by the A/D converter (not shown in the drawing) and is then supplied to the computer (not shown in the drawing). The computer generates image data based on the digital signal from the detection optical system 3 and outputs this image data on the monitor. Accordingly, a fluorescence image (a two-dimensional distribution of fluorescence luminance) of the sectional plane of the specimen A is provided to the user.

During this time, the control unit 10 raises and lowers the stage 18 in synchronization with the scanning of the scanning optical unit 13, which allows the examination surface in the specimen A to be moved as desired in the depth direction. Thus, it is possible to examine the state of cells in a sectional plane at a desired depth in the specimen A.

On the other hand, when commencing optical stimulus, the shutter 24, which is in the closed state, is opened by the control unit 10. By doing so, light from the lamp light source 21 is guided to the excitation filter 23 via the collector lens 22, and light in a predetermined wavelength band is transmitted therethrough. The light in the predetermined wavelength band is then guided to the variable aperture 25 via the shutter 24, is adjusted to a position and radiation region corresponding to the site to which the optical stimulus is to be applied, and irradiates the specimen A via the focusing lens 26 and the condenser lens 27. Accordingly, it is possible to simultaneously apply the optical stimulus to the entire specified site of the specimen A.

In this case, the control unit 10 controls the opening and closing of the shutter 24 in synchronization with the control of the scanning optical unit 13 in the observation scanning optical system 1 and the raising and lowering of the stage 8. Accordingly, it is possible to adjust the timing at which the optical stimulus is applied so that it is synchronized with the timing at which observation is performed (in other words, the three-dimensional scanning position of the observation laser light), which allows the optical stimulus to be applied at the desired observation timing. Furthermore, because the response can be observed immediately after the optical stimulus, it is possible to observe dynamic characteristics (chemical reactions) and so on in the specimen A caused by the light irradiation by the stimulus optical system 2.

Second Embodiment

Next, a microscope apparatus according to a second embodiment of the present invention will be described.

Figure 2:
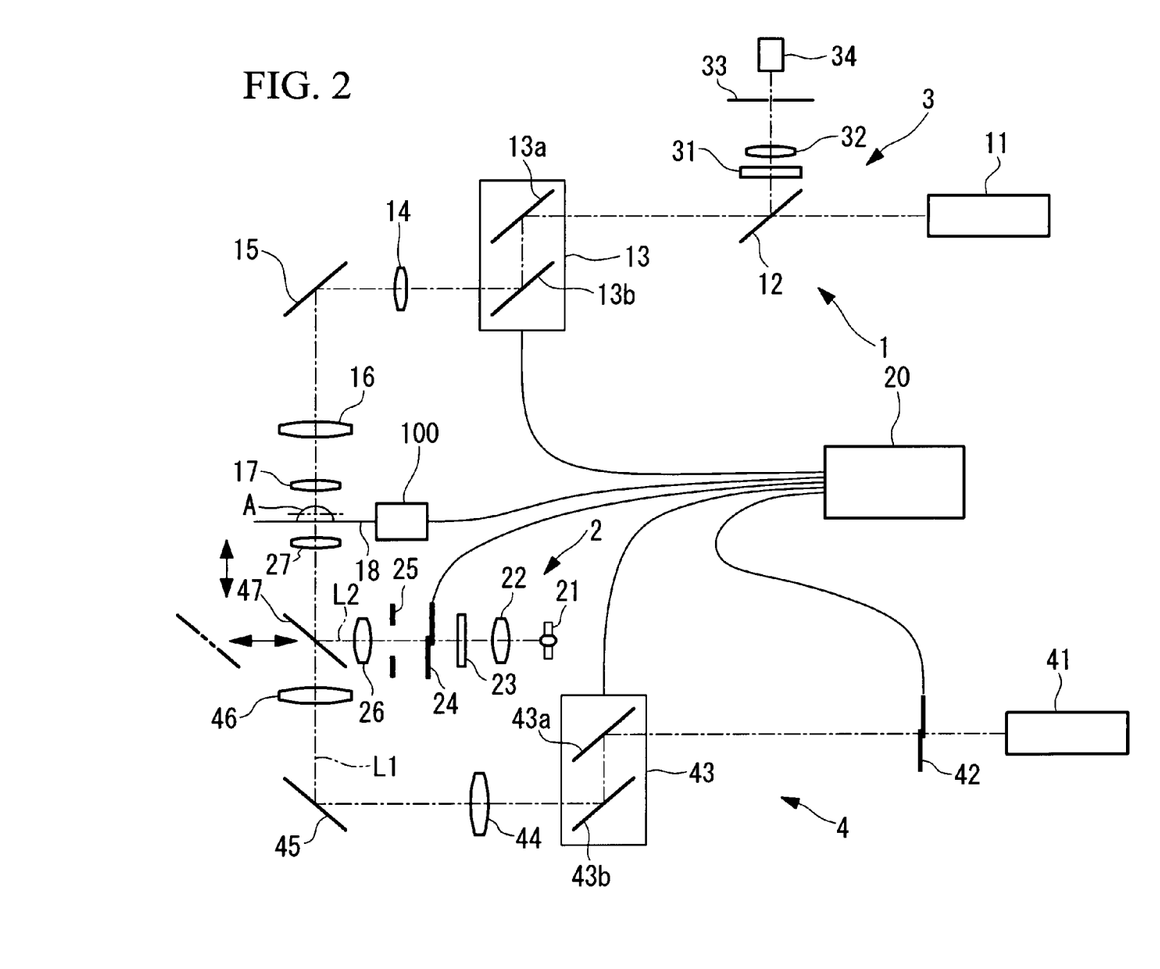
FIG. 2 is a diagram showing, in outline, the configuration of a microscope apparatus according to a second embodiment of the present invention.

FIG. 2 is a block diagram showing, in outline, the configuration of the microscope apparatus according to this embodiment. In this figure, elements that are the same as those in FIG. 1 are assigned the same reference numerals, and a description thereof is omitted.

As shown in FIG. 2, the microscope apparatus according to this embodiment has a configuration in which a stimulus scanning optical system 4 including a laser light source 41 is added to the configuration of the microscope apparatus shown in FIG. 1.

This stimulus scanning optical system 4 is formed of a laser light source 41 for emitting laser light, a shutter 42, a scanning optical unit 43, a relay lens 44, and a mirror 45. The scanning optical unit 43 is, for example, a galvanometer scanner formed of two opposingly disposed galvanometer mirrors 43a and 43b that can be oscillated back and forth about mutually orthogonal axes.

An image-forming lens 46, a dichroic mirror 47, and a condenser lens 27 are disposed in the path of the laser light reflected by the mirror 45. The dichroic mirror 47 is disposed at a position where a light path L1 of the laser light reflected by the mirror 45 intersects with a light path L2 of light emitted from the lamp light source 21 provided in the stimulus optical system 2. This dichroic mirror 47 has a construction whereby it is capable of being removed from and inserted into the light path L1. This dichroic mirror 47 has characteristics such that it transmits the light from the laser light source 41 and reflects the light from the lamp light source 21. The focal position of the relay lens 44 is located so as to be coincident with the focal position of the image-forming lens 46.

Reference numeral 20 in FIG. 2 is a control unit for synchronously controlling the scanning optical unit 13 of the observation scanning optical system 1, the shutter 24 of the stimulus optical system 2, the shutter 42 and the scanning optical unit 43 of the stimulus scanning optical system 4, and the focusing mechanism 100, which inserts and removes the dichroic mirror 47 into and from the light path L1 and which raises and lowers the stage 18.

When applying an optical stimulus with the stimulus scanning optical system 4 in the microscope apparatus having the above-described configuration, the shutter 42 is opened by the control unit 20. Accordingly, stimulus laser light emitted from the laser light source 41 is guided to the scanning optical unit 43 via the shutter 42 and is scanned by deflecting it in an arbitrary direction. Thereafter, the stimulus laser light travels along the path via the relay lens 44, the mirror 45, the image-forming lens 46, the dichroic mirror 47, and the condenser lens 27 and is focused onto a predetermined sectional plane of the specimen A, which is secured on the stage 18.

The entirety of an optical-stimulus target site defined within the predetermined sectional plane of the specimen A may be irradiated while scanning the laser light by continuously oscillating the galvanometer mirrors 43a and 43b, provided in the scanning optical unit 43, over a predetermined area under the control of the control unit 20. A predetermined optical stimulus position defined within the predetermined sectional plane of the specimen A may be irradiated with a spot by stopping the galvanometer mirrors 43a and 43b at predetermined angles under the control of the control unit 20. A plurality of arbitrary positions defined within the predetermined sectional plane of the specimen A may be momentarily irradiated with a spot of laser light by causing the galvanometer mirrors 43a and 43b to momentarily skip under the control of the control unit 20.

Once the optical stimulus applied by the stimulus scanning optical system 4 is completed, the laser light is blocked from entering the specimen A by closing the shutter 42 with the control unit 20.

When applying an optical stimulus with the stimulus optical system 2, by opening the shutter 24 with the control unit 20, the light emitted from the lamp light source 21 is guided to the excitation filter 23 via the collector lens 22. Light of a predetermined wavelength band transmitted by the excitation filter 23 is guided to the variable aperture 25 via the open shutter 24, is adjusted to a position and irradiation region according to the site to which the optical stimulus is to be applied, travels along the path via the focusing lens 26, the dichroic mirror 47, and the condenser lens 27, and irradiates the specimen A. Accordingly, it is possible to apply an optical stimulus over a wide area of the specimen A.

As described above, the microscope apparatus according to this embodiment includes the stimulus optical system 2, which is suitable for efficiently applying an optical stimulus over a wide area (for example, several tens to several hundreds of micrometers in diameter), and the stimulus scanning optical system 4, which is suitable for applying the optical stimulus in the form of a spot (for example, several micrometers in diameter) for a short period of time. Therefore, it is possible to switch between the optical systems used for optical stimulus according to the purpose. Thus, it is possible to achieve effective optical stimulus using the most appropriate optical system. Furthermore, not only do the laser light and the light emitted from the lamp light source have different irradiation regions, but their energy densities are also different. Therefore, it is also possible to use different stimulus times and response times in the specimen A, which enables the degrees of freedom of the optical stimulation to be increased.

By synchronously opening the shutters 14 and 23, it is possible to simultaneously irradiate the specimen A with the light from the lamp light source 21 and the laser light from the laser light source 22. Therefore, it is possible to provide optical stimulation with more variety.

Instead of the shutter 42 according to this embodiment, it is possible to provide an acousto-optic device.

Third Embodiment

Next, a microscope apparatus according to a third embodiment of the present invention will be described.

Figure 3:
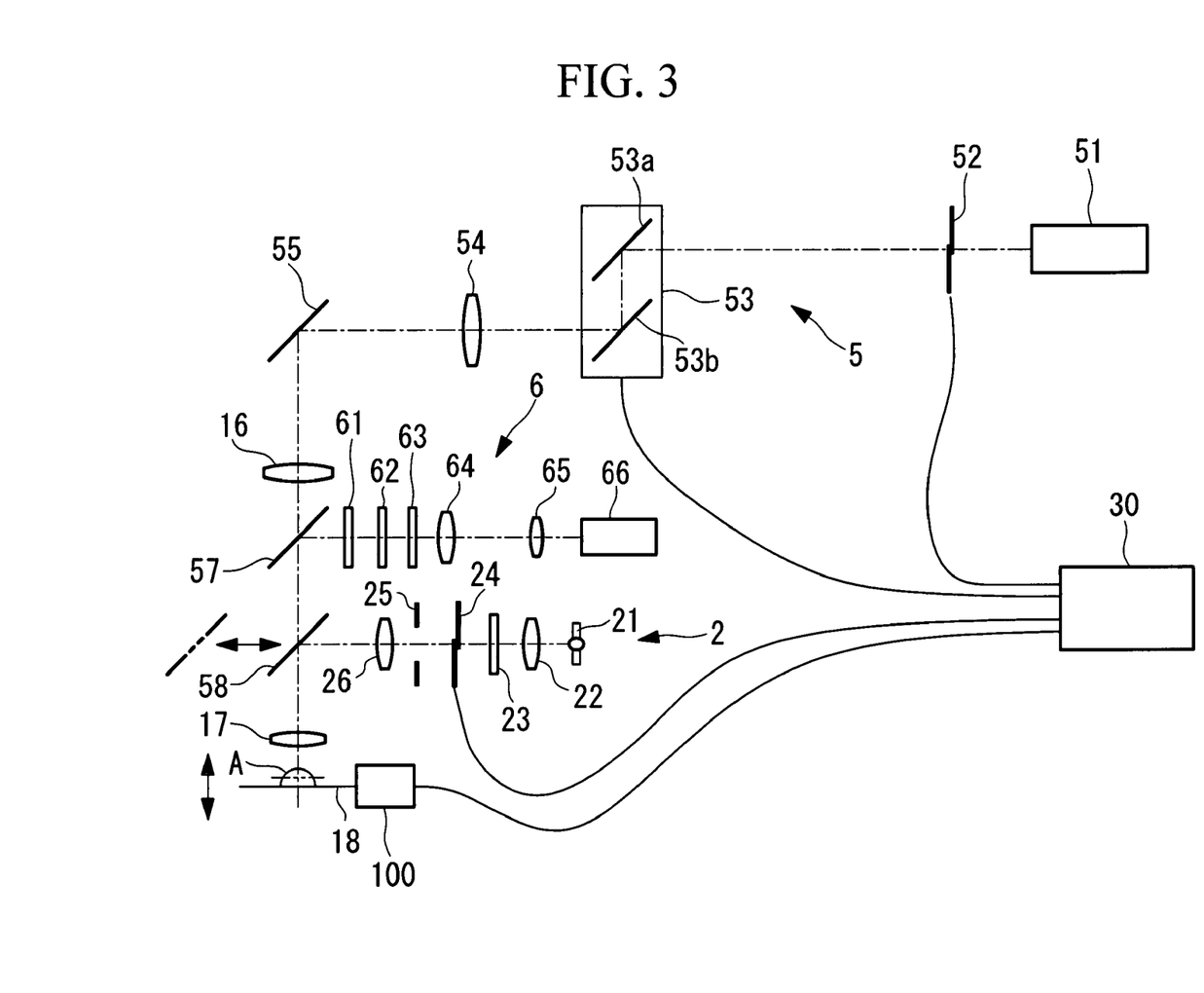
FIG. 3 is a diagram showing, in outline, the configuration of a microscope apparatus according to a third embodiment of the present invention.

FIG. 3 is a block diagram showing, in outline, the microscope apparatus according to this embodiment. In this figure, elements that are the same as those in FIG. 1 are assigned the same reference numerals, and a description thereof is omitted.

As shown in FIG. 3, the microscope apparatus according to this embodiment includes a multiphoton-excitation observation scanning optical system 5, a detection optical system 6, and a stimulus optical system 2. The microscope apparatus according to this embodiment has a configuration in which a light path of the observation optical system 5 and a light path of the stimulus optical system 2 are aligned at an intermediate part thereof, and the optical systems for observation and stimulation share a single objective lens 17.

The observation scanning optical system 5 includes a laser light source 51 which emits ultrashort pulsed laser light, a shutter 52, a scanning optical unit 53, a relay lens 54, and a mirror 55. The scanning optical unit 53 is, for example, a galvanometer scanner formed of two opposingly disposed galvanometer mirrors 53a and 53b which can be oscillated back and forth about mutually orthogonal axes.

Similarly to FIG. 1, an image-forming lens 16 and an objective lens 17 are disposed in the path of laser light reflected by the mirror 55, and dichroic mirrors 57 and 58 are disposed between the image-forming lens 16 and the objective-lens 17.

The dichroic mirror 57 is for guiding fluorescence excited by irradiating the specimen A with laser light from the laser light source 51 to the detection optical system 6. The dichroic mirror 57 has characteristics such that it transmits excitation light (near-infrared light) emitted from the laser light source 51 and reflects fluorescence (visible light) from the specimen.

The dichroic mirror 58 has characteristics such that it reflects stimulus light (violet or ultraviolet light) from the lamp light source 21, transmits excitation light (near-infrared light) from the laser light source 51, and transmits fluorescence (visible light) from the specimen A.

The detection optical system 6 includes a UV-cut filter 61, and an IR-cut filter 62, a bandpass filter 63 that transmits the wavelength component of the fluorescence, focusing lenses 64 and 65, and a photoelectric converting device 66. The UV-cut filter 61, the IR-cut filter 62, and the bandpass filter 63 extract from the light incident on the detection optical system 6 only the fluorescence produced in the specimen A and eliminate light of other wavelengths. Their characteristics are appropriately selected according to the wavelength of the light used as the optical stimulus, the wavelength of the observation laser light, and the wavelength of the fluorescence.

Reference numeral 30 in FIG. 3 is a control unit for synchronously controlling the shutters 52 and 24, the scanning optical unit 53, and the focusing mechanism 100 which raises and lowers the stage 18.

When performing observation with the microscope apparatus having the above-described configuration, the shutter 52 is opened by the control unit 30. The ultrashort pulsed laser light emitted from the laser light source 51 is guided to the scanning optical unit 53 via the open shutter 52 and is scanned by deflecting it in an arbitrary direction. Thereafter, the ultrashort pulsed laser light travels along the path including the relay lens 54, the mirror 55, the image-forming lens 16, the dichroic mirrors 57 and 58, and the objective lens 17, is focused onto a predetermined sectional plane of the specimen A, which is secured on the stage 18, and is two-dimensionally scanned within the sectional plane.

When irradiated with light in this way, a fluorescent indicator is excited by the light, producing fluorescence. The fluorescence from the specimen A travels in the opposite direction along substantially the same light path to a midpoint thereof; in other words, it is guided to the dichroic mirror 57 via the objective lens 17 and the dichroic mirror 48. Because the dichroic mirror 57 has characteristics such that it transmits excitation light (near-infrared light) from the laser light source 51 and reflects the fluorescence (visible light) from the specimen A, the fluorescence is reflected by the dichroic mirror 57 and is guided to the detection optical system 6.

In the detection optical system 6, by guiding the fluorescence to the UV-cut filter 61, the IR-cut filter 62, and the bandpass filter 63 and removing light of each specific wavelength, only the fluorescence produced in the sectional plane of the specimen A is selected and is made incident on the photoelectric converting device 66 via the focusing lenses 64 and 65. The brightness information measured by the photoelectric converting device 66 is output as an analog electrical signal to an A/D converter (not shown in the drawing) and is then sent to a computer, where the conditions in the sectional plane of the specimen A are provided to the user.

Next, when performing optical stimulus using the stimulus optical system 2, the shutter 24 is opened by the control unit 30. Accordingly, the stimulus light emitted from the lamp light source 21 is guided to the excitation filter 23 via the collector lens 22, where light of a predetermined wavelength band is selected and is guided to the variable aperture 25 via the open shutter 24. The stimulus light, which is adjusted to a predetermined area and a predetermined position by the variable aperture 25, is guided to the dichroic mirror 58 via the focusing lens 26. The stimulus light guided to the dichroic mirror 58 is combined with the observation laser light from the observation optical system 5 and irradiates a predetermined area of the specimen A via the objective lens 17.

The fluorescence excited in the specimen A is collected by the objective lens 17, passes through the dichroic mirror 58, is reflected by the dichroic mirror 57, and is guided to the detection optical system 6. In the detection optical system 6, by passing the light from the specimen A through the UV-cut filter 61, the IR-cut filter 62, and the bandpass filter 63, the excitation light reflected at the surface of the specimen due to fluorescence image deterioration and leakage light from the light used for stimulation are removed substantially completely, and only the desired fluorescence is guided to the photoelectric converting element 66 to be measured.

Accordingly, even when simultaneously performing optical stimulation and observation, it is possible to extract only the fluorescence component in the predetermined sectional plane of the specimen A, and it is thus possible to observe the specimen with high precision.

As described above, because the microscope apparatus of this embodiment uses the laser light source 51, which emits ultrashort pulsed laser light, as the light source which emits observation laser light, it is not necessary to provide a pinhole in the detection optical system 6, and the detection optical system 6 can be placed before the scanning optical unit 53 of the detection optical system. Accordingly, compared to the detection optical system 3 shown in FIG. 1, it is possible to reduce the number of lenses and reflecting surfaces between the detection optical system 6 and the specimen A. Therefore, it is possible to increase the intensity of the fluorescence incident on the photoelectric converting device 66, which allows the detection accuracy to be improved.

Because the detection optical system 6 includes the UV-cut filter 61, the IR-cut filter 62, and the bandpass filter 63, it is possible to remove the light used as the optical stimulus. Accordingly, it is possible to further increase the detection precision.

In addition, by providing a shared light path, from a certain intermediate point onwards, between the observation and stimulus functions, it is possible to reduce the overall size of the apparatus.

Instead of the shutter 42 according to this embodiment, an acousto-optic device may be provided.

Figure 4:
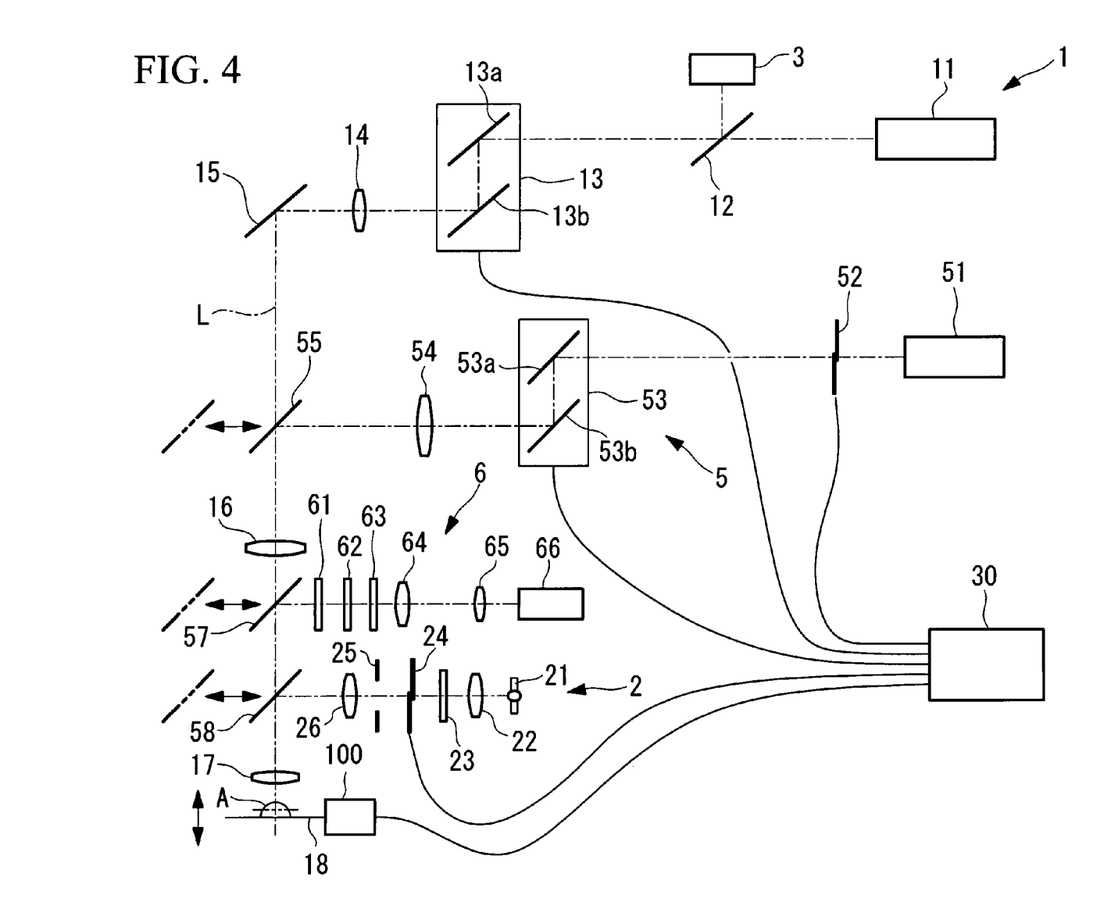
FIG. 4 is a diagram showing a modification of the microscope apparatus according to the third embodiment of the present invention.

As shown in FIG. 4, the microscope apparatus according to this embodiment may also be provided with a confocal observation scanning optical system 1 and a detection optical system 3. With this configuration, the mirror 55 and the dichroic mirror 57 are constructed so that they can be removed from and inserted into the light path. Thus, when using the confocal observation scanning optical system 1 as the observation optical system, by removing the mirror 55 and the dichroic mirror 57 from the light path L, the excitation light from the laser light source 11 is guided to the specimen A, and the fluorescence from the specimen A is guided to the detection optical system 3 along the same path as the excitation light described above. By closing the shutter 52 of the observation scanning optical system 5 at this time, the ultrashort pulsed laser light from the laser light source 51 is blocked.

In contrast, when using the observation scanning optical system 5 as the observation optical system, in other words, when performing observation with multiphoton excitation using the ultrashort pulsed laser, by inserting the mirror 55 and the dichroic mirror 57 into the light path L, the ultrashort pulsed laser light emitted from the laser light source 51 is guided to the specimen A. In such a case, the fluorescence produced in the specimen A passes through the dichroic mirror 58, is reflected by the dichroic mirror 57, and is guided to the detection optical system 6. In this case, the laser light source 11 of the observation scanning optical system 1 is turned off. The removal and insertion of the mirror 55 and the dichroic mirror 57 from and into the light path is carried out under the control of the control unit 30.

Fourth Embodiment

Next, a microscope apparatus according to a fourth embodiment of the present invention is described.

Figure 5:
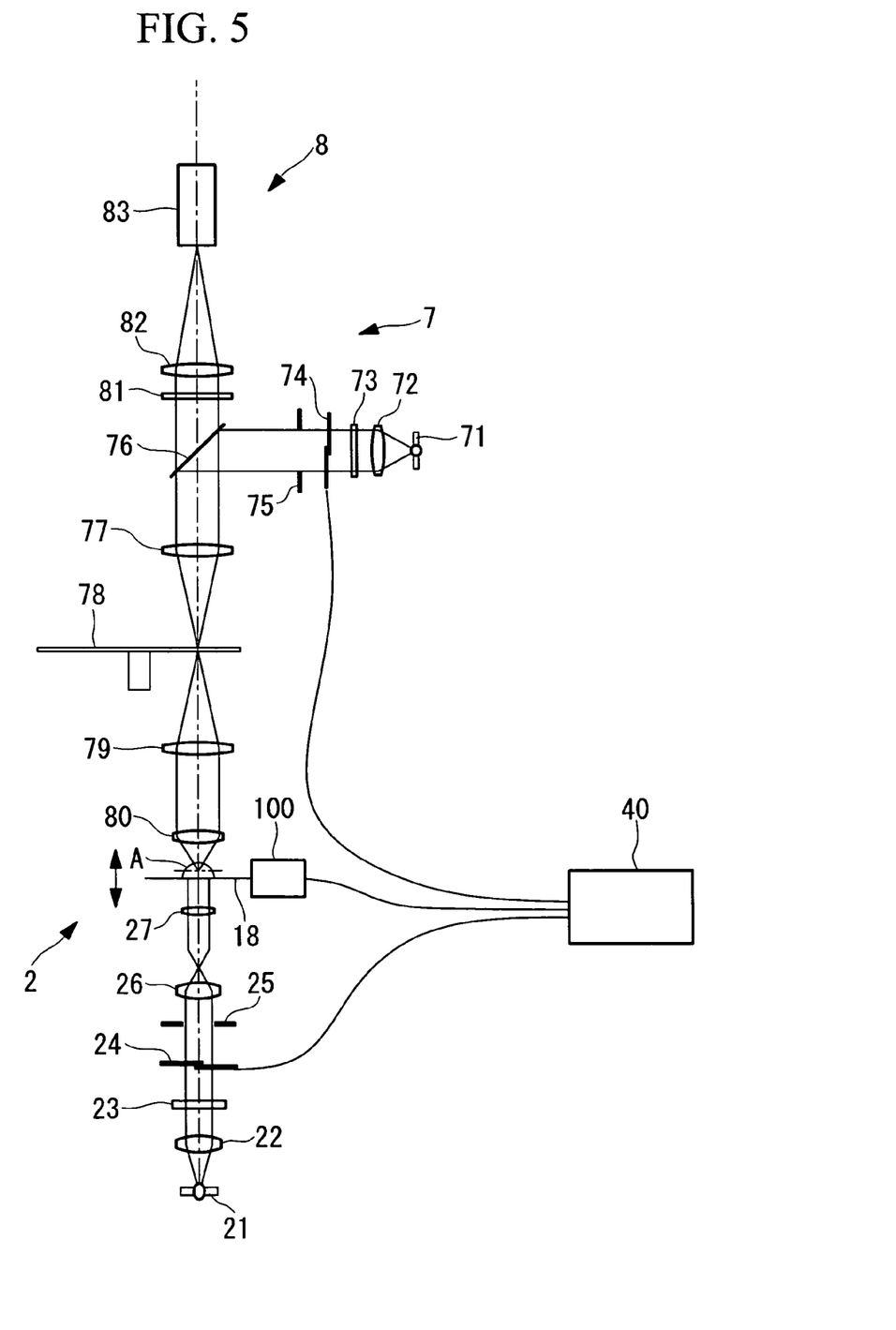
FIG. 5 is a diagram showing, in outline, the configuration of a microscope apparatus according to a fourth embodiment of the present invention.

FIG. 5 is a block diagram showing, in outline, the configuration of the microscope apparatus according to this embodiment. In this figure, elements that are the same as those in FIG. 1 are assigned the same reference numerals, and a description thereof is omitted.

As shown in FIG. 5, the microscope apparatus according to this embodiment includes a disc scanning optical system 7 and a stimulus optical system 2.

An irradiation portion of the disk scanning optical system 7 includes a lamp light source 71, a collector lens 72, an excitation filter 73, a shutter 74, a variable aperture 75, and a dichroic mirror 76.

The lamp light source 71 is, for example, a mercury lamp, a xenon lamp, a halogen lamp, a flash lamp, or the like. For example, when using GFP fluorescent protein, the excitation filter 73 has characteristics such that it transmits light of wavelengths ranging from about 460 to 480 nm.

The dichroic mirror 76 has characteristics such that it reflects the excitation light emitted from the lamp light source 71 and transmits fluorescence from the specimen A. A relay lens 77, a confocal disk 78, an image-forming lens 79, and an objective lens 80 are disposed in the path of light reflected by the dichroic mirror 76. The confocal disk 78 is positioned such that the plane of its substrate is substantially orthogonal to the optical axis and is constructed so as to be capable of rotating about an axis parallel to the optical axis. The confocal disk 78 is located at the focal positions of the relay lens 77 and the image-forming lens 79, so that the focal position of the objective lens 80 and the position of the confocal disk 78 are conjugate with each other.

A plurality of pinholes or a slit having a width approximately equal to that of the pinholes is formed in the confocal disk 78. By rotating it, the excitation light passing through the pinholes or slit is scanned on the specimen A.

A detection portion 8 of the disk scanning optical system 7, which is provided in the path of the light transmitted through the dichroic mirror 76, includes an absorption filter 81, an image-forming lens 82, and an image-acquisition unit 83.

In FIG. 5, reference numeral 40 is a control unit for synchronously controlling the shutter 24 provided in the stimulus optical system 2, the focusing mechanism 100 for raising and lowering the stage 18, and the shutter 74 provided in the disk scanning optical system 7.

When carrying out observation using the disk scanning optical system 7 in the microscope apparatus having the configuration describe above, the shutter 74 is opened by the control unit 40. Accordingly, the observation light (excitation light) emitted from the lamp light source 71 is guided to the excitation filter 73 via the collector lens 72, where light of a predetermined wavelength band is selected and then guided to the variable aperture 75 via the open shutter 74. The observation light adjusted by the variable aperture 75 is reflected by the dichroic mirror 76 and is guided to the confocal disk 78 via the relay lens 77. The observation light passing through the pinholes or slit provided in the confocal disk 78 passes through the image-forming lens 79 and the objective lens 80, is scanned on the specimen A, and excites fluorescence.

The fluorescence from the specimen A travels along the path including the objective lens 80, the image-forming lens 79, the confocal disk 78, the relay lens 77, and the dichroic mirror 76, and enters the detection portion 8. Of the light entering the detection portion 8, components other than the fluorescence are removed by the absorption filter 81, and the fluorescence wavelength component is guided to the image-acquisition unit 83 via the image-forming lens 82.

As describe above, because the microscope apparatus according to this embodiment performs observation using the observation optical system which includes the disk scanning optical system 7, it is possible to obtain information about a sectional plane of the specimen A at high speed and over a wide area. It is thus possible to observe a response over a wide area immediately after applying the optical stimulus.

Although the embodiments of the present invention have been described with reference to the drawings, the specific construction is not limited to these embodiments; the present invention also includes various modifications so long as they do not depart from the spirit of the invention.

For example, it is possible to use any arbitrary combination of the respective optical systems in the embodiments described above. For example, instead of the observation scanning optical system 1 shown in FIG. 1, it is possible to use the observation scanning optical system 5 shown in FIG. 3. In such a case, the detection optical system should be changed depending on the observation optical system. Also, instead of the observation optical system 5 shown in FIG. 3, the observation optical system 1 or the observation optical system 7 may be employed. Furthermore, the microscope apparatuses shown in FIGS. 3 and 4 may be configured to include the stimulus scanning optical system 4.

Regarding the position of the observation optical system 2 and the stimulus scanning optical system 4, as shown in FIG. 3, it is also possible to place the observation optical system so that so that parts of the light paths are aligned and the shared objective lens 17 is used. Or, as shown in FIGS. 1 and 4, the light path may be separated from the light path of the observation optical system and may be disposed at the opposite side of the specimen A. When both the stimulus optical system 2 and the stimulus scanning optical system 4 are provided, it is possible to adopt a configuration in which, for one of the stimulus optical systems, an optical stimulus may be applied from the same direction as the observation optical system, and for the other stimulus optical system, the optical stimulus may applied from a different direction from the observation optical system.

The microscope apparatuses described above may include two or more observation optical systems. In this case, the optical system used for observation may be switched depending on the application.

Applications of the optical stimulus in the microscope apparatus of the present invention include, for example, cage release in caged compounds, photobleaching in fluorescence recovery after photo-bleaching (FRAP), acceptor photobleaching in fluorescence resonant energy transfer (FRET), and so forth.

What is claimed is:

1. A microscope apparatus comprising:
   at least one observation scanning optical system including a laser light source for emitting observation laser light, an objective lens, and a scanning optical system for two-dimensionally scanning the observation laser light in a predetermined examination plane of a specimen via the objective lens;
   a detection optical system for detecting fluorescence produced by irradiating the specimen with the observation laser light;
   at least one stimulus optical system which includes a lamp light source for emitting light having a wavelength used for optical stimulation and a shutter in a light path between the lamp light source and the specimen, and which irradiates the specimen with the light emitted from the lamp light source;
   a light-path combining device for simultaneously guiding both the observation laser light and the light used for optical stimulation to the objective lens, the light-path combining device being provided between the objective lens and the shutter such that the microscope apparatus is capable of irradiating the specimen with the light used for optical stimulation emitted from the stimulus optical system via the objective lens by opening the shutter while the specimen is irradiated with the observation laser light via the objective lens and then detecting the fluorescence by the detection optical system, and the light combining device being adapted to combine the observation laser light with the light used for optical stimulation by transmitting one of the observation laser light and the light used for optical stimulation and reflecting the other;
   a focusing mechanism for adjusting a distance between the specimen and the objective lens; and
   a control unit for synchronously controlling the scanning optical system provided in the observation scanning optical system, the shutter provided in the stimulus optical system, and the focusing mechanism;
   wherein the control unit controls opening and closing of the shutter provided in the stimulus optical system in accordance with a scanning timing of the observation laser light by the observation scanning optical system, thereby enabling a response of the specimen to be observed by the detection optical system immediately after an optical stimulus applied by irradiation of the light used for optical stimulation emitted from the lamp light source; and wherein the detection optical system includes a filter for eliminating light in a wavelength band used for the optical stimulation.

2. A microscope apparatus according to claim 1, further comprising at least one stimulus scanning optical system including a laser light source for emitting laser light used for optical stimulation and a scanning optical system for two-dimensionally scanning the laser light in a predetermined sectional plane of the specimen.

3. A microscope apparatus according to claim 2, wherein the stimulus scanning optical system includes a shutter in a light path between the laser light source and the specimen.

4. A microscope apparatus according to claim 1, further comprising a detection device for detecting fluorescence generated by performing multiphoton excitation on the specimen; and a dichroic mirror for splitting off the fluorescence from an illumination light path into a light path of the detection device, the dichroic mirror being disposed between a scanning optical unit and the objective lens;

wherein the laser light source comprises an ultrashort pulsed laser light source for emitting light having a near-infrared wavelength.

* * * * *